(12) United States Patent
Masters et al.

(10) Patent No.: US 12,115,019 B2
(45) Date of Patent: Oct. 15, 2024

(54) ULTRASONIC IMAGING SYSTEM AND METHOD

(71) Applicant: SoundCath, Inc., Canoga Park, CA (US)

(72) Inventors: Donald Masters, Sylmar, CA (US); Jesus Andres Lopez, III, Bloomington, CA (US)

(73) Assignee: SoundCath, Inc., Canoga Park, CA (US)

( * ) Notice: Subject to any disclaimer, the term of this patent is extended or adjusted under 35 U.S.C. 154(b) by 101 days.

(21) Appl. No.: 17/813,903

(22) Filed: Jul. 20, 2022

(65) Prior Publication Data

US 2024/0023933 A1    Jan. 25, 2024

(51) Int. Cl.
*A61B 8/00* (2006.01)
*A61B 8/08* (2006.01)
*A61B 8/12* (2006.01)
*A61B 90/00* (2016.01)
*B06B 1/02* (2006.01)
*B06B 1/06* (2006.01)

(52) U.S. Cl.
CPC ............ *A61B 8/445* (2013.01); *A61B 8/0883* (2013.01); *A61B 8/12* (2013.01); *A61B 8/4488* (2013.01); *A61B 8/5207* (2013.01); *A61B 90/39* (2016.02); *B06B 1/0215* (2013.01); *B06B 1/0622* (2013.01); *A61B 2090/3966* (2016.02); *B06B 2201/76* (2013.01)

(58) Field of Classification Search
CPC ....................................................... A61B 8/12
See application file for complete search history.

(56) References Cited

U.S. PATENT DOCUMENTS

| | | | | |
|---|---|---|---|---|
| 5,954,654 | A * | 9/1999 | Eaton | A61M 25/0136 600/459 |
| 2008/0208121 | A1* | 8/2008 | Youssef | A61B 18/1492 604/114 |
| 2009/0088648 | A1* | 4/2009 | Jaffe | A61B 5/0084 600/466 |
| 2011/0257523 | A1* | 10/2011 | Hastings | A61B 18/0206 601/2 |
| 2014/0276084 | A1* | 9/2014 | Kemp | A61B 8/12 600/467 |

(Continued)

*Primary Examiner* — Colin T. Sakamoto
*Assistant Examiner* — Tommy T Ly
(74) *Attorney, Agent, or Firm* — Nelson Mullins Riley & Scarborough LLP

(57) ABSTRACT

An ultrasonic imaging system is disclosed. The ultrasonic imaging system comprises an ultrasonic catheter having a longitudinal axis, a proximal end, and a distal end. The ultrasonic imaging system includes an ultrasonic transducer array disposed within the distal end of the ultrasonic catheter. The ultrasonic transducer array comprises a plurality of transducer array elements arranged on a substrate. Further, a catheter shaft is connected at one end to a handle assembly and at other end to the ultrasonic transducer array. The catheter shaft houses an electronic flex cable which is in communication with at least one signal trace, and is configured to direct each of the plurality of transducer array elements to transmit and receive ultrasound beams, receive at least one signal from the plurality of transducer array elements, and construct at least one image of at least a portion of the heart based on the at least one signal.

20 Claims, 9 Drawing Sheets

(56) References Cited

U.S. PATENT DOCUMENTS

| | | | |
|---|---|---|---|
| 2015/0265245 A1* | 9/2015 | von Ramm | B06B 1/0625 |
| | | | 600/443 |
| 2016/0199030 A1* | 7/2016 | Patil | A61B 8/4411 |
| | | | 600/459 |
| 2018/0344283 A1* | 12/2018 | Rice | A61B 8/12 |
| 2019/0053783 A1* | 2/2019 | Stigall | A61B 8/56 |
| 2020/0061340 A1* | 2/2020 | Mixter | A61M 25/0147 |
| 2020/0330072 A1* | 10/2020 | Jacobs | A61B 8/12 |
| 2021/0030394 A1* | 2/2021 | Caswell | A61B 8/4472 |
| 2022/0048071 A1* | 2/2022 | Sudol | H01L 24/46 |

* cited by examiner

ULTRASONIC IMAGING SYSTEM AND METHOD

FIELD OF THE DISCLOSURE

The present disclosure relates generally to the field of ultrasonic imaging systems. More particularly, some embodiments relate to ultrasonic catheters connected to an ultrasonic imaging system, for acquiring two-dimensional image information.

BACKGROUND OF THE DISCLOSURE

Use of catheter-based structural and electrophysiological procedures have recently expanded to more complex scenarios, in which an accurate definition of variable individual cardiac anatomy is a key to obtain optimal results. Intracardiac echocardiography (ICE) is a unique imaging modality for high-resolution real-time visualization of cardiac structures, continuous monitoring of catheter location within the heart, and early recognition of procedural complications, such as pericardial effusion or thrombus formation. Further, ICE imaging modality includes additional benefits, such as excellent patient tolerance, reduction of fluoroscopy time, and elimination of need for general anaesthesia or second operator. Currently, ICE imaging modality has largely replaced trans-oesophageal echocardiography as ideal imaging modality for guiding certain procedures, such as atrial septal defect closure and catheter ablation of cardiac arrhythmias, and has an emerging role in others, including mitral valvuloplasty, transcatheter aortic valve replacement, and left atrial appendage closure.

In electrophysiology procedures, ICE imaging modality allows integration of real-time images with electro-anatomic maps. ICE imaging modality has a role in assessment of arrhythmogenic substrate and is particularly useful for mapping structures that are not visualized by fluoroscopy, such as the interatrial or interventricular septum, papillary muscles, and intracavitary muscular ridges. For these reasons, ICE has largely replaced trans-oesophageal echocardiography (TEE). Further, the introduction of ICE represents a major advancement in cardiac imaging and has become an integral part of a variety of percutaneous interventional and electrophysiology procedures, potentially improving outcomes and reducing risks. ICE allows a real-time assessment of cardiac anatomy during interventional procedures and guides catheter manipulation in relation to the different anatomic structures.

In contrast to TEE, ICE is performed by the primary operator of the interventional procedure under conscious sedation, without the need for endotracheal intubation, and thereby eliminate the risk of oesophageal trauma and other post anaesthesia outcomes. In addition, ICE reduces fluoroscopy exposure to both the patient and the operator, may improve outcomes, shortens the procedure time, and facilitates early recognition of complications such as thrombus formation or pericardial effusion. Therefore, there is a need for an improved ultrasonic imaging system using an ultrasonic ICE catheter.

SUMMARY OF THE DISCLOSURE

By way of introduction, the preferred embodiments described below include an easy-to-use ultrasonic imaging system is disclosed. The ultrasonic imaging system comprises an ultrasonic catheter having a longitudinal axis, a proximal end, and a distal end. Further, an ultrasonic transducer array is disposed of within the distal end of the ultrasonic catheter. The ultrasonic transducer array comprises a plurality of transducer array elements arranged on a substrate. It can be noted that the plurality of transducer array elements corresponds to a micro-electromechanical (MEMS) based Piezoelectric Micromachined Ultrasonic Transducer (pMUT). Further, the ultrasonic imaging system comprises a catheter shaft connected at one end to a handle assembly and at other end to the ultrasonic transducer array. The catheter shaft encloses an electronic flex cable which is in communication with at least one signal trace and is configured to: direct each of the plurality of transducer array elements, via the at least one signal trace, to transmit and receive, with respect to heart, ultrasound beams having a bandwidth including a predetermined fundamental mode vibration of each of the plurality of transducer array elements, such that a single array element can transmit and receive multiple fundamental mode vibrations simultaneously; receive at least one signal from the plurality of transducer array elements based on transmitting and receiving at least one ultrasound beam of the ultrasound beams, and construct at least one image of at least a portion of the heart based on the at least one signal.

Further, the ultrasonic imaging system comprises an imaging device coupled to the ultrasonic catheter using a custom dongle. The custom dongle is coupled to the handle assembly using an interposer and a flat circuit board. The custom dongle is configured to communicate ultrasound transmit pulses and ultrasound receive waveforms between the ultrasonic catheter and the imaging device. Further, the ultrasonic imaging system comprises a steering control unit positioned within the handle assembly for articulating a distal tip of the ultrasonic catheter and aligning the face of the ultrasonic transducer array towards internal views including an anterior position or a posterior position of the heart. It can be noted that the distal tip of the ultrasonic catheter is coated with a material to provide electrical isolation and transmission of ultrasound signals.

In one embodiment, an ultrasonic catheter is disclosed. The ultrasonic catheter comprises a body having a longitudinal axis and a distal end. Further, an ultrasonic transducer array is disposed within the distal end of the body. The ultrasonic transducer array comprises a plurality of transducer array elements arranged on a substrate. It can be noted that the plurality of transducer array elements corresponds to a micro-electromechanical (MEMS) based Piezoelectric Micromachined Ultrasonic Transducer (pMUT). Further, each of the plurality of transducer array elements comprises individual elements of multiple diameters. Further, the ultrasonic transducer array is connected in series between at least one signal trace and a common ground. Further, each transducer array element comprises a plurality of transducers, with a first group of two or more transducers in a first transducer array element and a second group of two or more transducers in the first transducer array element. Further, each of the plurality of transducer array elements are connected in parallel. Further, at least one first electrode is connected between the at least one piezoelectric layer and a signal conductor, and at least one second electrode is connected between the at least one piezoelectric layer and a ground conductor.

In one embodiment, an intracardiac echocardiographic (ICE) imaging system is disclosed. The ICE imaging system comprises an ultrasonic catheter having a longitudinal axis, a proximal end, and a distal end. Further, a micro-electromechanical system (MEMS) based Piezoelectric Micromachined Ultrasonic Transducer (pMUT) array is disposed of within the distal end of the ultrasonic catheter. The MEMS based pMUT array comprises a plurality of MEMS based pMUT array elements arranged on a substrate. Further, the ultrasonic imaging system comprises an electronic flex cable connected at one end to a handle assembly and at other end to the MEMS based pMUT array. The electronic flex cable is in communication with at least one signal trace and is configured to: direct each of the plurality of MEMS based pMUT array elements, via the at least one signal trace, to transmit and receive, with respect to heart, ultrasound beams; receive at least one signal from the plurality of MEMS based pMUT array elements based on transmitting and receiving at least one ultrasound beam of the ultrasound beams, and construct at least one image of at least a portion of the heart based on the at least one signal.

Other features and aspects of this disclosure will be apparent from the following description and the accompanying drawings.

BRIEF DESCRIPTION OF THE DRAWINGS

The accompanying drawings illustrate various embodiments of systems, methods, and embodiments of various aspects of the disclosure. Any person of ordinary skill in the art will appreciate that the illustrated element boundaries (e.g., boxes, groups of boxes, or other shapes) in the figures represent one example of the various boundaries representative of the disclosed invention. It may be that in some examples one element may be designed as multiple elements or that multiple elements may be designed as one element. In other examples, an element shown as an internal component of one element may be implemented as an external component in another and vice versa. Furthermore, elements may not be drawn to scale. Non-limiting and non-exhaustive descriptions of the present disclosure are described with reference to the following drawings. The components in the figures are not necessarily to scale, emphasis instead being placed upon the illustrated principles.

Various embodiments will hereinafter be described in accordance with the appended drawings, which are provided to illustrate and not to limit the scope of the disclosure in any manner, wherein similar designations denote similar elements, and in which.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

Some embodiments of this disclosure, illustrating all its features, will now be discussed in detail. The words "comprising," "having," "containing," and "including," and other forms thereof, are intended to be equivalent in meaning and be open-ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems, and methods are now described. The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Embodiments of the present disclosure will be described more fully hereinafter with reference to the accompanying drawings in which like numerals represent like elements throughout the several figures, and in which example embodiments are shown. Embodiments of the present disclosure may, however, be embodied in alternative forms and should not be construed as being limited to the embodiments set forth herein. The examples set forth herein are non-limiting examples and are merely examples among other possible examples.

Figure 1:
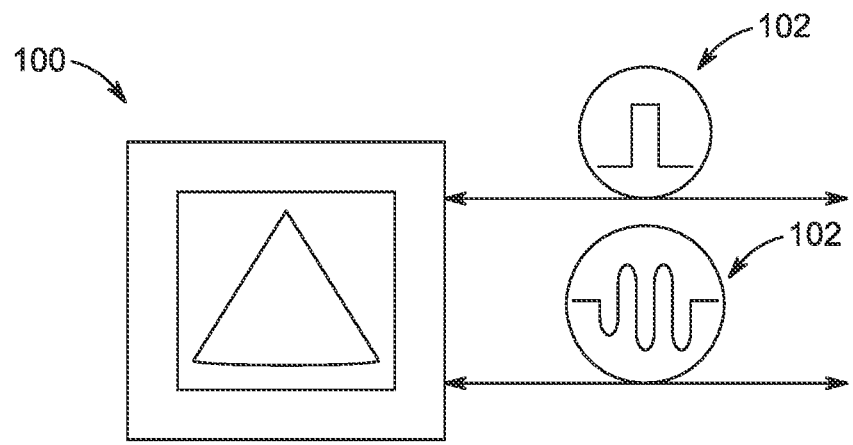
FIGS. 1 and 2 illustrate a prior art imaging system, for acquiring two-dimensional image information.
Figure 2:
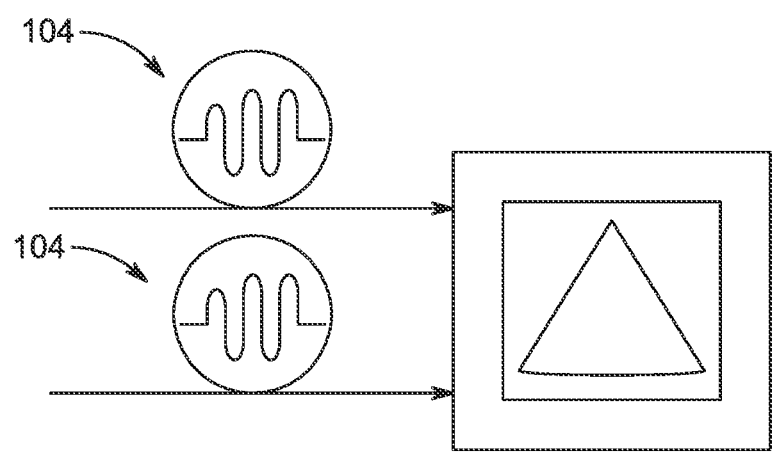

FIGS. 1 and 2 illustrate a prior art imaging system 100. The imaging system 100 may be used for diagnosis and/or treatment in combination with another imaging modality, such as an x-ray, fluoroscopy, magnetic resonance, computed tomography, or optical system. It can be noted that imaging modalities scan a patient for generating images to assist a physician. Further, the imaging system 100 provides an ultrasound transmit pulse 102 and an ultrasound receive path 104, for connection to an ultrasonic transducer (not shown). The ultrasound transmit pulse 102 may transmit ultrasound signals from the imaging system 100 towards an object such as heart of a patient. Further, the ultrasound receive path 104 may create a waveform based at least on the ultrasound signals. Thereafter, the imaging system 100 may convert the received ultrasound signals or ultrasound information to a two-dimensional (2D) image of the object or a portion of the object.

Figure 3:
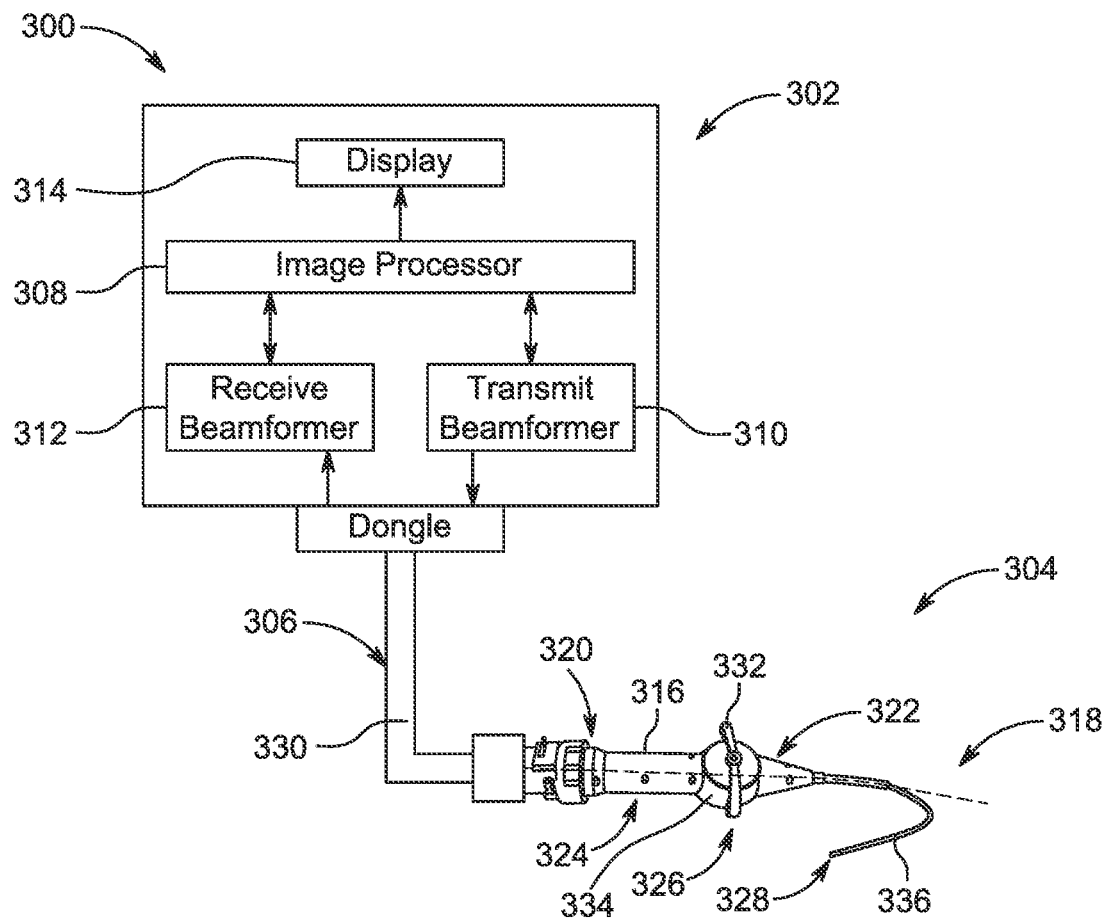
FIG. 3 illustrates a schematic diagram of an ultrasonic imaging system, according to an embodiment of the present disclosure.

FIG. 3 illustrates a schematic diagram of an ultrasonic imaging system 300, according to an embodiment of the present disclosure. FIG. 3 is described in conjunction with FIGS. 4-12.

The ultrasonic imaging system 300 may be performed for electrophysiology (EP). The ultrasonic imaging system 300 may be used for diagnosis and/or treatment in combination with another imaging modality, such as an x-ray, fluoroscopy, magnetic resonance, computed tomography, or optical system. Both imaging modalities may scan a patient for generating images to assist a physician. The data from the different modalities may be aligned by locating the markers with a known spatial relationship to the ultrasound scan in the images of the other modality. In other embodiments, the ultrasonic imaging system 300 may use a catheter without the markers and/or without another imaging modality. In one embodiment, the ultrasonic imaging system 300 may utilize a microelectromechanical (MEMS) transducer array defined as piezoelectric micro-machined ultrasound transducer (pMUT) or other types of MEMS transducers, interconnected using matched flexible circuits. In one embodiment, the ultrasonic imaging system 300 may correspond to an intracardiac echocardiographic (ICE) imaging system. In one embodiment, the ultrasonic imaging system 300 may correspond to an endovascular MEMS ultrasonic transducer utilizing a high-density flexible circuit for all transmission and electrical interconnects. In one embodiment, the ultrasonic imaging system 300 may be employed to treat patient with cystic fibrosis (CF). It can be noted that the use of the high-density flexible circuits may enable highly repeatable and stable transmission and return signals. Further, the high density flexible circuit transmission lines may transmit electrical energy from one end to another distal end of the ultrasonic imaging system 300.

Referring to FIG. 3, the ultrasonic imaging system 300 may comprise an imaging device 302 coupled to an ultrasonic catheter 304 via a communication channel 306. In one embodiment, the communication channel 306 may be a custom dongle with a cable and bus connections or multiple connections. Hereinafter, the communication channel 306 may be referred to as the custom dongle 306.

The ultrasonic catheter 304 may be disposed within a chamber of a heart of a patient and the imaging device 302 may receive at least one signal from the ultrasonic catheter 304. The at least one signal may be communicated from the ultrasonic catheter 304 to the imaging device 302 via the custom dongle 306. Further, the imaging device 302 may comprise an image processor 308, a transmit beamformer 310, a receive beamformer 312, and a display 314.

The image processor 308 may be configured to generate a two-dimensional (2D) image according to data received from the ultrasonic catheter 304. In one embodiment, the image processor 308 may be configured to receive a focused signal from the receive beamformer 312. The image processor 308 may render the data to construct an image or sequence of images. In one embodiment, the image may be three dimensional (3D) representation, such as a two-dimensional image rendered from a user or a processor selected viewing direction. In one embodiment, the image processor 308 may be a detector, filter, processor, application-specific integrated circuit, field-programmable gate array, digital signal processor, control processor, scan converter, three-dimensional image processor, graphics processing unit, analog circuit, digital circuit, or combinations thereof. The image processor 308 may receive beamformed data and may generate images, to display on the display 314. It can be noted that the generated images are associated with a two-dimensional (2D) scan. Alternatively, the generated images may be three-dimensional (3D) representations.

The image processor 308 may be programmed for hardware accelerated two-dimensional re-constructions. The image processor 308 may store processed data of the at least one signal and a sequence of images in a memory. In one embodiment, the memory may be a non-transitory computer-readable storage media. The instructions for implementing the processes, methods and/or techniques discussed herein are provided on the computer-readable storage media or memories, such as a cache, buffer, RAM, removable media, hard drive, or other computer-readable storage media. Non-transitory computer-readable storage media include various types of volatile and non-volatile storage media. The functions, acts, or tasks illustrated in the figures or described herein are executed in response to one or more sets of instructions stored in or on a computer readable storage media. The functions, acts, or tasks are independent of the particular type of instructions set, storage media, processor, or processing strategy and may be performed by software, hardware, integrated circuits, firmware, micro code, and the like, operating alone or in combination.

The transmit beamformer 310 may be configured for transmission of the electrical signal or electrical impulse in a form of at least one signal towards the ultrasonic catheter 304. The receive beamformer 312 may be configured to receive an electrical signal or electrical impulse from the ultrasonic catheter 304. In one embodiment, the transmit beamformer 310 and the receive beamformer 312 may facilitate transmit beamforming technique to focus energy towards a receiver to improve a signal to noise (SNR) of the at least one signal and then transmit the at least one signal to the image processor 308.

The display 314 may be configured to screen the image or sequence of images during or after the data is rendered, by the image processor 308. The image may be three dimensional (3D) representation, such as a two-dimensional image rendered from a user or a processor selected viewing direction. Alternatively, the image may be one or more two-dimensional images representing planes in the volume. In one embodiment, the display 314 may be a part of imaging device 302 or may be remote, such as a networked display. In one embodiment, the display 314 may be a cathode ray tube (CRT), liquid crystal display (LCD), a projector, a plasma, or other now known or later developed display device.

The ultrasonic catheter 304 may be in electronic communication with the imaging device 302 for transmission and receiving of ultrasound signals to and from an arterial wall of a vascular system. In one embodiment, the ultrasonic catheter 304 may be configured to visualize standard echocardiography views of the heart, such as in a standard version, a right atrium may be visualized. The visualizations performed using the ultrasonic catheter 304 is described in conjunction with FIGS. 13 and 14. The ultrasonic catheter 304 may be employed in transseptal catheterization for several percutaneous interventions, including left heart catheter ablation, atrial septal defect closure for effective alternative to surgical intervention. Further, the ultrasonic catheter 304 may comprise a body 316 having a longitudinal axis 318, a proximal end 320, a distal end 322, a handle assembly 324, a steering control unit 326, a distal tip 328, and a dongle cable 330.

Figure 6A:
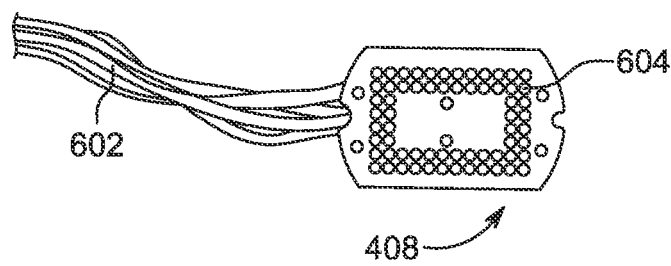
FIG. 6A illustrates a flat circuit board with an electronic flex cable, according to an embodiment of the present disclosure.
Figure 6B:
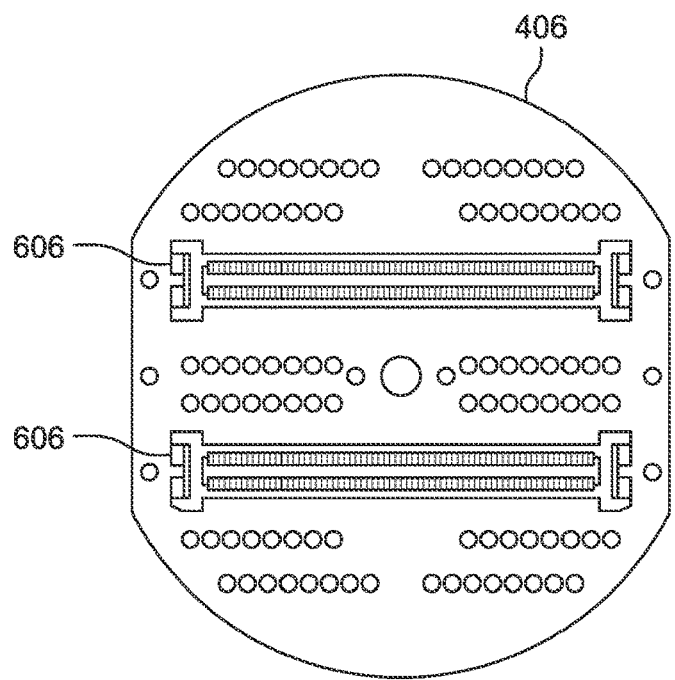
FIG. 6B illustrates a proximal view of an interposer with a board edge connector disposed within the custom dongle, according to an embodiment of the present disclosure.
Figure 6C:
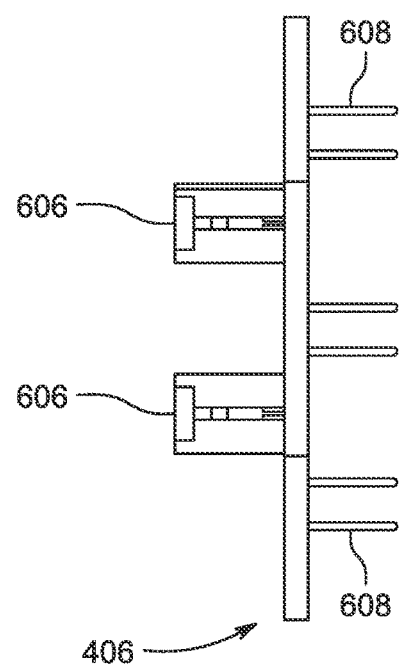
FIG. 6C illustrates a side view of the interposer with a plurality of inline connectors and circuit pins disposed over a printed circuit board (PCB), according to an embodiment of the present disclosure.
Figure 6D:
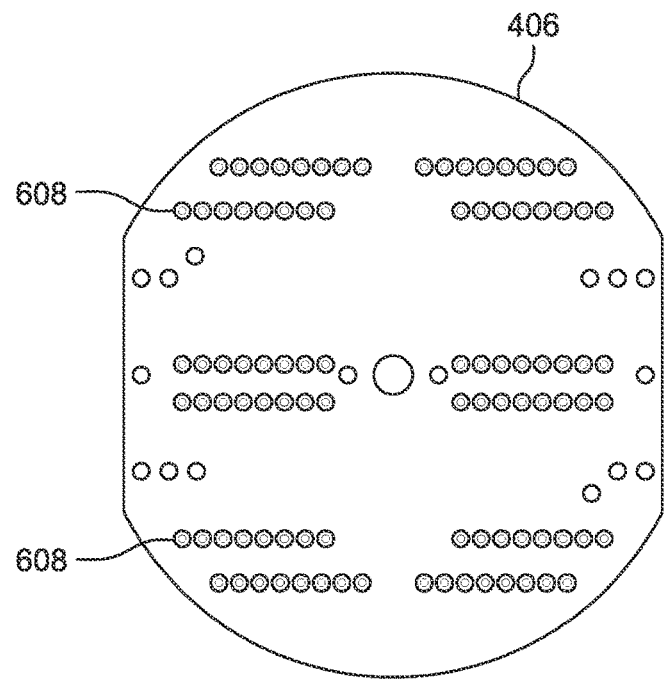
FIG. 6D illustrates a distal view of the interposer with the circuit pins to couple the interposer with electronic flex cables in the custom dongle, according to an embodiment of the present disclosure.

The handle assembly 324 may be positioned between the proximal end 320 and the distal tip 328 of the ultrasonic catheter 304. Further, the steering control unit 326 may be positioned within the handle assembly 324. The steering control unit 326 may be provided for articulating the distal tip 328 of the ultrasonic catheter 304. Further, the steering control unit 326 may align face of an ultrasonic transducer array (not shown) towards different positions with respect to the ultrasonic catheter 304. Further, the steering control unit 326 may comprise a steering handle 332 and a housing 334 enclosing an actuator (not shown) and a steering hub (not shown). It can be noted that an internal friction occurs between the actuator and the steering hub, and between the actuator and the housing 334, which causes the ultrasonic catheter 304 to retain its adjusted configuration without operator attention. The steering handle 332 may be rotated to facilitate positioning of the distal tip 328 of the ultrasonic catheter 304. The movement of the distal tip 328 by the steering control unit 326 is shown in FIG. 7. In one embodiment, the steering handle 332 may be rotated to position the distal tip 328 inside the chamber of the heart of the patient. In one embodiment, the steering control unit 326 may comprise a set of steering lines controlled by a steering actuator to articulate bidirectional a distal segment of the ultrasonic catheter 304. It can be noted that the steering handle 332 may be rotated from 0 degrees to +/−45 degrees. A catheter shaft 336 may be coupled to the handle assembly 324 at one end and to the distal tip 328 of the ultrasonic catheter 304 at the other end. Further, the catheter shaft 336 may enclose an electronic flex cable (not show) and a plurality of steering cables (not shown). In one embodiment, the electronic flex cable may be a stainless steel cable. The electronic flex cable may be coupled at one end to the handle assembly 324 and at other end to the ultrasonic transducer array. The electronic flex cable and the plurality of steering cables may be described later in conjunction with FIGS. 6A-7. Further, the ultrasonic catheter 304 is described in conjunction with FIG. 4.

Figure 4:
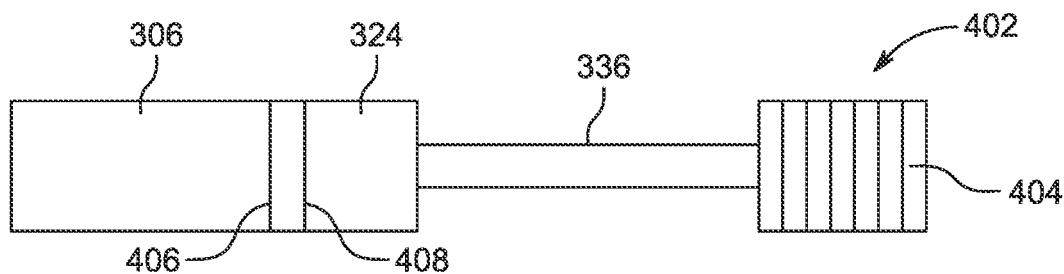
FIG. 4 illustrates a schematic diagram of a front view of an ultrasonic catheter and a custom dongle, according to an embodiment of the present disclosure.

Referring to FIG. 4, the ultrasonic catheter 304 may comprise an ultrasonic transducer array 402, a substrate 404, an interposer 406, and a flat circuit board 408. The ultrasonic transducer array 402 may be disposed within the distal tip 328 of the ultrasonic catheter 304. In one embodiment, the ultrasonic transducer array 402, the substrate 404, the interposer 406, and a flat circuit board 408 may correspond to flexible printed electronic circuits for communicating from the distal end 322 of the ultrasonic catheter to the dongle cable 330 or directly to the ultrasonic imaging system 300. The ultrasonic transducer array 402 may be disposed over the substrate 404 towards the distal end 328 of the ultrasonic catheter 304. It can be noted that the ultrasonic transducer array 402 may correspond to MEMS based pMUT array. The handle assembly 324 may be coupled to the proximal end 320 of the ultrasonic catheter 304, using the interposer 406 and the flat circuit board 408. In one embodiment, the handle assembly 324 may be coupled to the dongle cable 330 using a catheter handle (not shown) and the interposer 406. The catheter handle will be described later in conjunction with FIG. 6B to FIG. 6D. It can be noted that the interposer 406 may be coupled to the custom dongle 306 and the flat circuit board 408 may be coupled to the proximal end 320 of the ultrasonic catheter 304, towards the handle assembly 324.

As shown in FIGS. 3-4, the catheter shaft 336 may be coupled between the handle assembly 324 and the ultrasonic transducer array 402. The electronic flex cable inside the catheter shaft 336 may receive the at least one signal from the ultrasonic transducer array 402 and the received signal may be communicated back to imaging device 302 via the custom dongle 306. The electronic flex cable may be coupled at one end to the handle assembly 324 and at other end to the ultrasonic transducer array 402. It can be noted that the ultrasonic transducer array 402 may receive electrical signals from the imaging device 302 via the custom dongle 306 and the electronic flex cable. It can also be noted that the ultrasonic transducer array 402 may transmit the at least one signal back to the imaging device 302 to further analyze the at least one signal for image generation. Further, the ultrasonic catheter 304 may be coupled to the ultrasonic imaging device 302 using the dongle cable 330. Further, the interposer 406 and the flat circuit board 408 may be coupled together using circuit pins of male ends and female ends, as shown in FIG. 5 and FIG. 6A.

Figure 5:
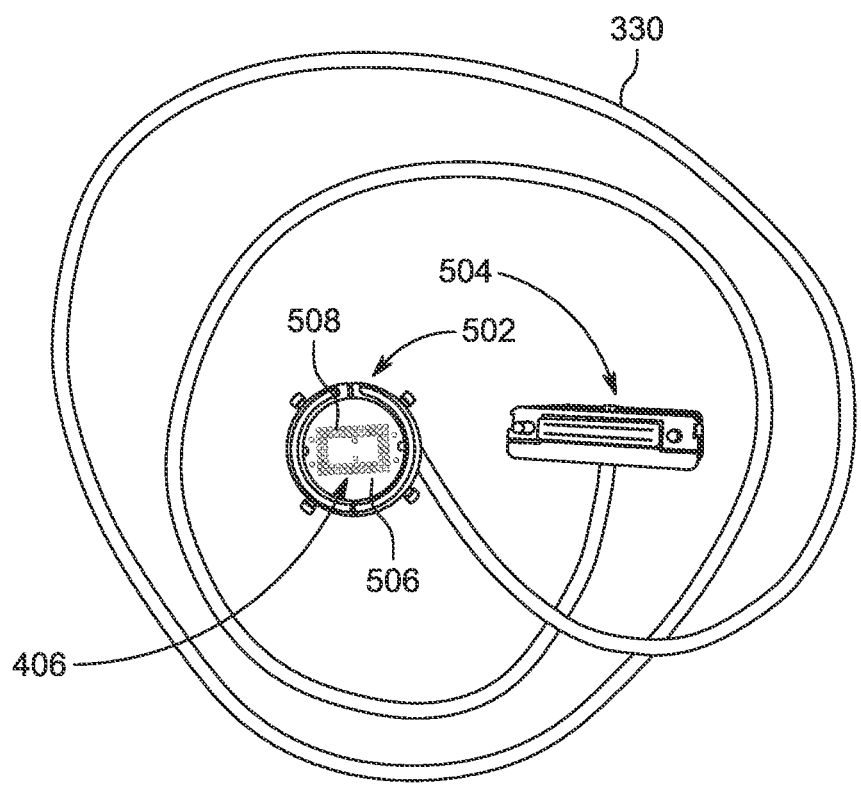
FIG. 5 illustrates a perspective view of the custom dongle for connecting the ultrasonic catheter and the imaging device, according to an embodiment of the present disclosure.

Referring to FIG. 5, a perspective view of the custom dongle 306 for communication between the ultrasonic catheter 304 and the imaging device 302 is disclosed, according to an embodiment of the present disclosure. It can be noted that the custom dongle 306 is the communication channel to transmit and receive electrical energy or electrical impulses between the distal tip 328 of the ultrasonic catheter 304 and the imaging device 302. The custom dongle 306 may comprise a dongle handle end 502, the dongle cable 330, and a dongle instrument end 504. The dongle handle end 502 may be coupled to the handle assembly 324 of the ultrasonic catheter 304, using the interposer 406 and the flat circuit board 408. In one embodiment, the dongle handle end 502 may receive the interposer 406, and the handle assembly 324 may hold the flat circuit board 408.

As shown in FIG. 5, the interposer 406 may comprise a printed board 506 and a plurality of pogo pins 508 disposed over the printed board 506. It can be noted that the plurality of pogo pins 508 may act as male attachment points, to be coupled with the flat circuit board 408. As shown in FIG. 6A, the flat circuit board 408 may be coupled to an electronic flex cable 602. The flat circuit board 408 may comprise a plurality of landing pads 604. The plurality of landing pads 604 may be disposed over the flat circuit board 408. The plurality of landing pads 604 may be configured to receive the plurality of pogo pins 508. It can be noted that the plurality of landing pads 604 of the flat circuit board 408 may be press-fitted into the plurality of pogo pins 508 of the printed board 506. The electronic flex cable 602 coupled at one end to the flat circuit board 408 may be coupled at other ends to the distal end 322 of the ultrasonic catheter 304. Further, the dongle instrument end 504 may be coupled to the imaging device 302. The imaging device 302 may receive the at least one signal and the acoustic echo from the ultrasonic transducer array 402 via the dongle cable 330.

Further, the ultrasonic catheter 304 may be provided to transmit ultrasound signals inside a subject. In one embodiment, the ultrasonic catheter 304 may be a flexible elongate member with the body 316 having the longitudinal axis 318, the proximal end 320, and the distal end 322. Further, the body 316 may comprise the ultrasonic transducer array 402 disposed within the distal end 322 of the ultrasonic catheter 304.

Figure 6E:
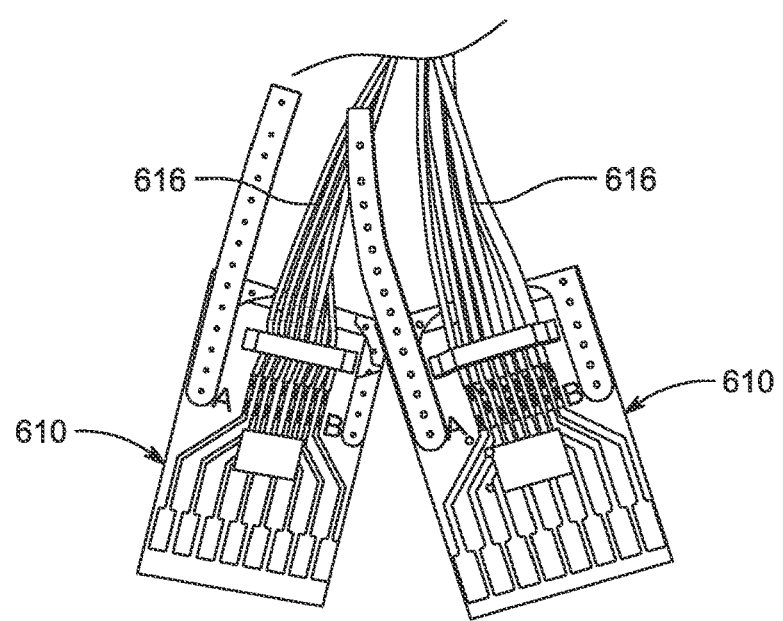
FIG. 6E illustrates the PCB which connects to the interposer, according to an embodiment of the present disclosure.

Referring to FIGS. 6B-6E, the interposer 406 with board edge connectors 606 disposed within the custom dongle 306 towards the dongle handle end 502, is disclosed. The board edge connectors 606 may correspond to inline printed circuit board (PCB) connectors. In one embodiment, the board edge connectors 606 are standard board edge connectors mounted in a round PCB within the custom dongle 306 towards the dongle handle end 502. The interposer 406 may comprise connector pins 608 towards the proximal view, which allow connection by soldering to the dongle cable 330 inside the custom dongle 306. Further, the board edge connectors 606 may be disposed over the interposer 406 from one side and the connector pins 608 may be disposed over the interposer 406 from other side. In one embodiment, the connector pins 608 may be detachably coupled to the dongle cable 330 using different soldering connections. In another embodiment, the board edge connectors 606 may be detachably coupled to the handle assembly 324 using a PCB 610, as shown in FIGS. 6E-6F.

Figure 6F:
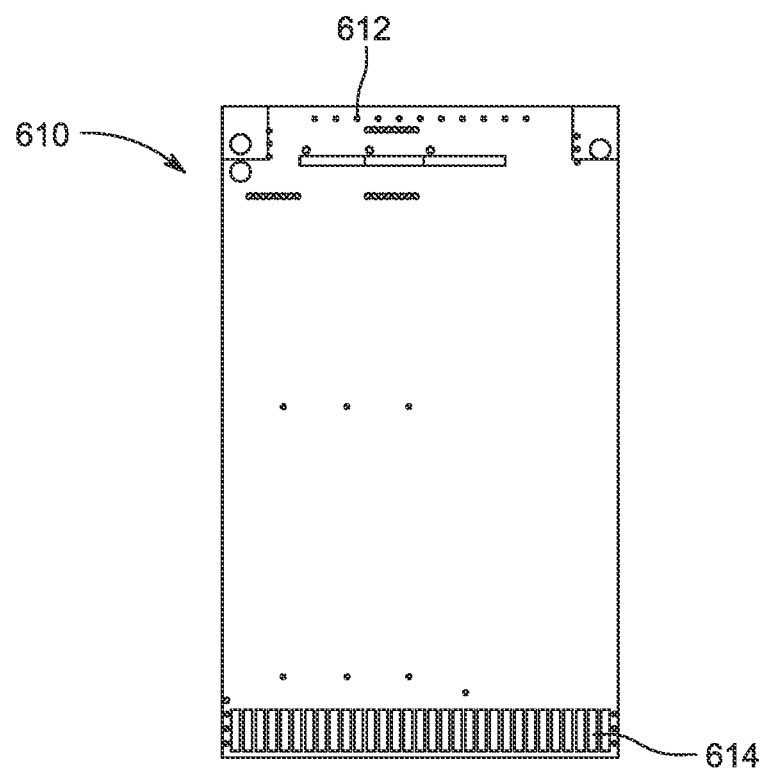
FIG. 6F illustrates the PCB located in a catheter handle with a plurality of inline connection pads, according to an embodiment of the present disclosure.
Figure 7:
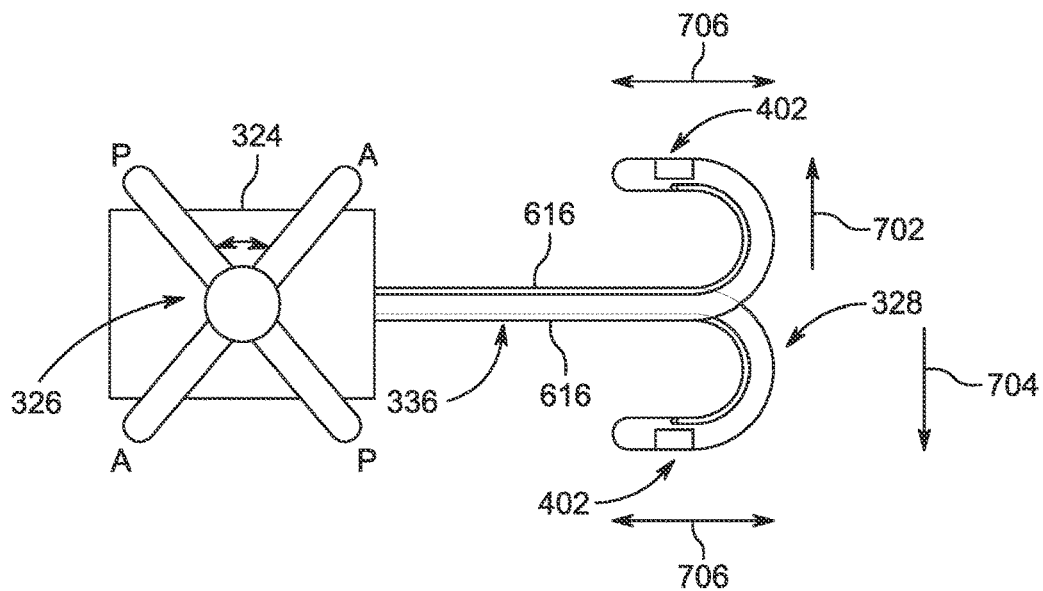
FIG. 7 illustrates a schematic view of the ultrasonic catheter with a distal tip being diverted to an anterior position and a posterior position using a steering control unit, according to an embodiment of the present disclosure.

The handle assembly 324 may comprise the PCB 610 towards the proximal end 320 of the ultrasonic catheter 304, as shown in FIGS. 6E-6F. Further, the PCB 610 may comprise a plurality of vias 612 disposed at one side of the PCB 610 and a plurality of inline connection pads 614 disposed at other side of the PCB 610. Further, the plurality of inline connection pads 614 may be disposed within the board edge connectors 606 of the interposer 406. It can be noted that the plurality of inline connection pads 614 may be grooved sections of rectangular shape. The board edge connectors 606 may receive the plurality of inline connection pads 614, when the dongle handle end 502 of custom dongle 306 is coupled to the handle assembly 324, towards the proximal end 320 of the ultrasonic catheter 304. In one embodiment, the plurality of inline connection pads 614 of the PCB 610, may mate with the board edge connectors 606 of the interposer 406, at one end. In another embodiment, the plurality of vias 612, may be used to terminate connection of the catheter shaft 336, at other end. It can be noted that the plurality of vias may correspond to a plurality of pads. Further, plurality of vias 612 of the PCB 610 may be configured to receive a plurality of steering cables 616.

Further, the custom dongle 306 may be coupled to the handle assembly 324 using the interposer 406 and the flat circuit board 408 disposed between the custom dongle 306 and the handle assembly 324. In one embodiment, the custom dongle 306 may be coupled to the handle assembly 324 using the board edge connectors 606. The custom dongle 306 may be configured to communicate ultrasound transmit pulses and ultrasound receive waveforms to the ultrasonic transducer array 402. In one embodiment, the interposer 406 and the flat circuit board 408 may be referred to as a flexible circuit interposers and catheter shaft 336 may be referred to as a flexible circuit transmission line. It can be noted that the at least one signal may be electrical energy transmitted to and/or from the catheter shaft 336 and the interposer 406 from the proximal end 320 to the distal end 322 of the ultrasonic catheter 304. Further, the ultrasonic transducer array 402, disposed within the distal end 322 of the ultrasonic catheter 304, may convert the electrical energy into an-acoustic pressure wave. Further, the acoustic echo may be converted back to electric energy and may be returned through the catheter shaft 336 from the distal end 322 to the proximal end 320 of the ultrasonic catheter 304. The electrical energy or electrical pulse may be transmitted to the imaging device 302 for processing within the image processor 308.

In one embodiment, the catheter shaft 336, the interposer 406, the flat circuit board 408, and the substrate 326 may be ultra-high density flexible circuits that may be primarily constructed of high ductility copper on a polyimide base substrate. It can be noted that ground return and electromagnetic interference (EMI) shielding may be integrated into the flexible circuit transmission lines. In one embodiment, the catheter shaft 336 attachment to the ultrasonic transducer array 402 may utilize thermo-compression adhesives and/or various metallic solders. It can be noted that the use of flexible circuits such as catheter shaft 336, the interposer 406, the flat circuit board 408, and the substrate 404, minimizes errors that would typically be associated with traditional small gauge coaxial cables utilized in many modern-day imaging catheters.

Referring to FIG. 7, a schematic view of the ultrasonic catheter 304 with the distal tip 328 being diverted to an anterior position 702 and a posterior position 704 using the steering control unit 326 is disclosed, according to an embodiment of the present disclosure.

The steering control unit 326 may be positioned within the handle assembly 324 for articulating the distal tip 328 of the ultrasonic catheter 304 and for aligning the face of the ultrasonic transducer array 402 towards internal view including, the anterior position 702 or the posterior position 704 of the heart. It can be noted that the distal tip 328 of the ultrasonic catheter 304 may correspond to a tip of the catheter shaft 336 of the ultrasonic catheter 304. Further, the ultrasonic transducer array 402 may be disposed of within the distal tip 328 of the ultrasonic catheter 304. It can be noted that a cable connecting the distal end 322 of the catheter handle to the distal tip 328 may be the catheter shaft 336. In one embodiment, the ultrasonic transducer array 402 may be positioned towards the internal views including anterior position 702 and the posterior position 704 of the heart. The distal tip 328 of the ultrasonic catheter 304 may be curved towards the distal end 322. In one embodiment, the distal tip 328 of the ultrasonic catheter 304 may be coated with a material to provide electrical isolation and transmission of ultrasound signals. Further, the catheter shaft 336 in communication between the distal tip 328 and the distal end 322 of the ultrasonic catheter 304, may transmit electrical signals or pulses to the distal tip 328 of the ultrasonic catheter 304, and the ultrasonic transducer array 402 may transmit back acoustic echo to the imaging device 302 via the catheter shaft 336 and the custom dongle 306.

The plurality of steering cables 616 may be diverted to the anterior position and the posterior position using the steering control unit 326, as shown in FIG. 7. The plurality of steering cables 616 may be housed within the catheter shaft 336. In one embodiment, at least two steering cables of the plurality of steering cables 616 may be diverted towards at least two distal tips with ultrasonic transducer arrays, using the steering control unit 326. Further, the catheter shaft 336 having a gradient durometer 706 of Pebax material towards the distal tip 328 of the ultrasonic catheter 304. It can be noted that the gradient durometer 706 of Pebax material may be hard and rigid towards the proximal end 320 and softer towards the distal end 322 of the catheter shaft 336. In one embodiment, the catheter shaft 336 may be softer for at least 6 to 8 inches towards the distal end 322. It can be noted that the distal tip 328 may have the softer Pebax material. Further, the plurality of steering cables 616 may be configured to bend or tilt the distal tip 328, when the steering handle of the steering control unit 326 is rotated clockwise or counter clockwise. It can be noted that the actuator of the steering control unit 326 may pull a steering cable of the plurality of steering cables 616, when inserted inside the heart. The steering cable of the plurality of steering cables 616 may then bend the distal tip 328 towards the anterior position and the posterior position inside the heart. In one embodiment, at least two steering cables of the plurality of steering cables 616 may be bent using the steering control unit 326.

In one embodiment, the plurality of steering cables 616 can be made of synthetic materials, such as nylon or similar synthetic fibres, or plastics material, such as urethane, Teflon®, Kynar®, Kevlar®, polyethylene, multi-stranded nylon, or gel-spun polyethylene fibres. For example, the plurality of steering cables 616 may be a multi-stranded Spectra® brand nylon line sold as Spiderwire® fishing line (10 lbs. test).

Figure 8:
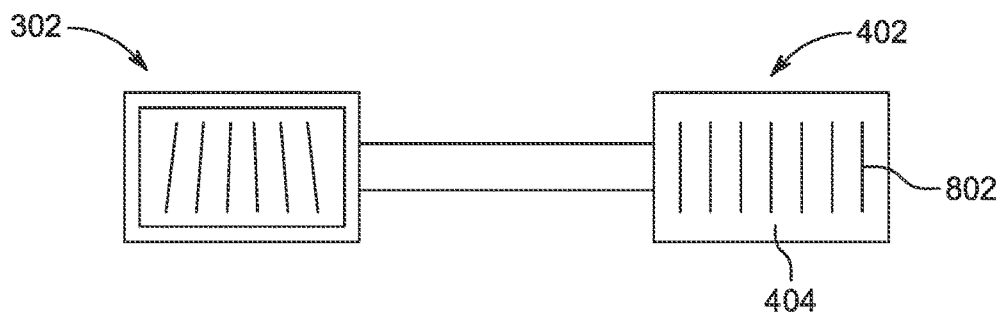
FIG. 8 illustrates a multi-channel electronic communication between the imaging device and an ultrasonic transducer array of the ultrasonic catheter, according to an embodiment of the present disclosure.

Referring to FIG. 8 a multi-channel electronic communication between the ultrasonic imaging device 302 and the ultrasonic transducer array 402 is disclosed, according to an embodiment of the present disclosure. The ultrasonic transducer array 402 may comprise a plurality of transducer array elements 802 arranged on the substrate 404. Further, each of the plurality of transducer array elements 802 may provide a wide bandwidth of an individual focused beam. The ultrasonic transducer array 402 may be coupled to the ultrasonic imaging device 302 using the dongle cable 330, as described earlier. The MEMS based ultrasonic transducer array 402 disposed within the distal end 322 of the ultrasonic catheter 304 may transmit the at least one signal via the electronic flex cable 602 inside the catheter shaft 336 to the imaging device 302. The at least one signal may be the acoustic echo transmitted from the ultrasonic transducer array 402. It can be noted that the acoustic echo of acoustic energy may be received from a face of the ultrasonic transducer array 402 and received at the image processor 308.

Further, the plurality of steering cables 616 may be configured to direct each of the plurality of transducer array elements 802, via the at least one signal trace, to transmit and receive, ultrasound beams. The ultrasound beams may have a bandwidth including a predetermined fundamental mode vibration of each of the plurality of transducer array elements 802, such that a single array element can transmit and receive multiple fundamental mode vibrations simultaneously. It can be noted that the plurality of transducer array elements 802 may transmit and receive the ultrasound beams with respect to the heart or at least a portion of the heart. Further, the electronic flex cable 602 inside the catheter shaft 336 may be configured to receive at least one signal from the plurality of transducer array elements 802 based on transmitting and receiving at least one ultrasound beam of the ultrasound beams. The imaging device 302 may be further configured to construct at least one image of at least the portion of the heart based on the at least one signal. It can be noted that the electronic flex cable may be configured to the transmit beamformer 310 and receive beamformer 312 to display a two-dimensional (2D) image information of the heart or the at least portion of the heart.

In one embodiment, the plurality of transducer array elements 802 may correspond to a micro-electromechanical (MEMS) based Piezoelectric Micromachined Ultrasonic Transducers (pMUTs). The catheter shaft 336 may be connected to the handle assembly 324 at one end and to the ultrasonic transducer array 402 at other end. The electronic flex cable 602 inside the catheter shaft 336 may be in communication with the at least one signal trace. It can be noted that the electronic flex cable 602 may be further communicate to the transmit beamformer 310 and the receive beamformer 312, via the custom dongle 306 to display a two-dimensional (2D) image information of the heart to be scanned.

Figure 9:
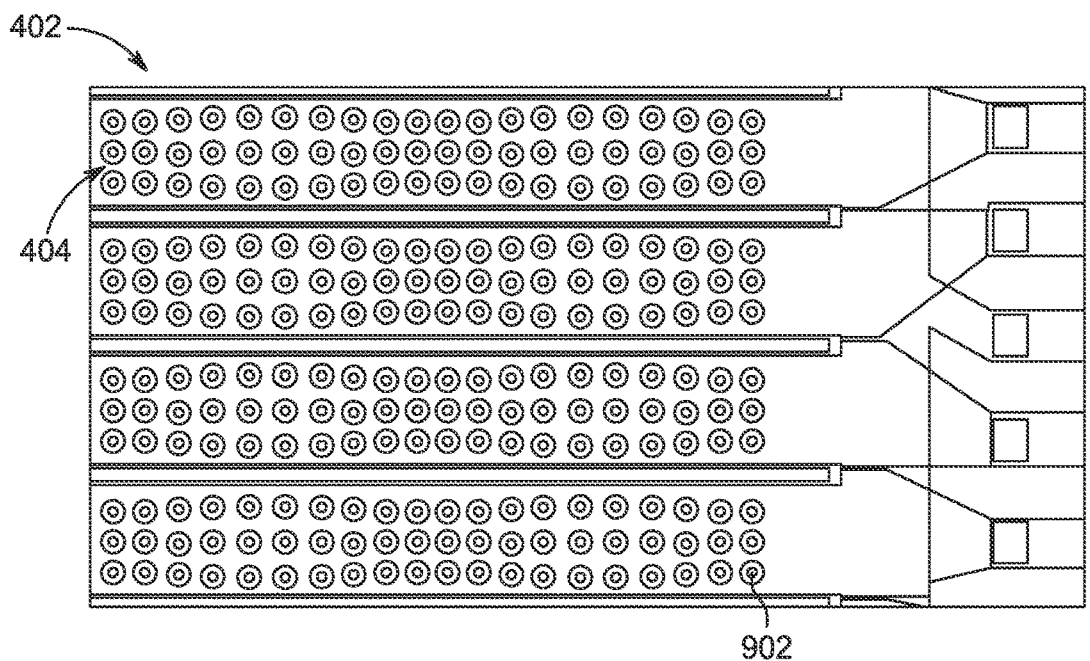
FIG. 9 illustrates a sectional view of a distal end of the ultrasonic catheter with a plurality of transducer array elements, according to an embodiment of the present disclosure.

Referring to FIG. 9, a sectional view of the distal end 322 of the ultrasonic catheter 304 having the ultrasonic transducer array 402 with the plurality of transducer array elements 802, is disclosed, according to an embodiment of the present disclosure. The distal end 322 of the ultrasonic catheter 304 may be provided with the ultrasonic transducer array 402 having the plurality of transducer array elements 802. Further, each of the plurality of transducer array elements 802 may have a plurality of individual transducer cells 902 arranged in a manner to provide a wide bandwidth of the individual focused beam. In one embodiment, the ultrasonic transducer array 402 may be constructed from a pMUT array containing individual elements of different diameters. In one embodiment, to achieve wider bandwidth with pMUT arrays, multiple diameters of pMUT cells may be integrated into one element. It can be noted that by arranging pre-shaped pMUTs with different diameters, a broader bandwidth can be realized through the complex interaction between the individual pMUT elements. In one embodiment, the pMUT cells of multiple diameters may achieve a bandwidth of greater than 55%. For example, in 3 elements, there are 5 different dome diameters, and each array is of a different size, such as 300 μm.

Further, the ultrasonic transducer array 402 may correspond to pMUT and the plurality of transducer array elements 802 may correspond to a plurality of pMUT elements. In one embodiment, the plurality of pMUT elements may be directed to transmit and receive, the ultrasound beams having the bandwidth including the predetermined fundamental mode vibration of each of the plurality of pMUT elements, such that a single pMUT element can transmit and receive multiple fundamental mode vibrations simultaneously. Further, the electronic flex cable 602 inside the catheter shaft 336 receives the at least one signal from the plurality of pMUT elements. It can be noted that the at least one signal may correspond to the at least one ultrasound beam. The at least one signal may be transmitted to the ultrasonic imaging device 302 for further processing in the image processor 308. The image processor 308 may construct the at least one image of the heart. It can be noted that the plurality of pMUT elements may be used to create the individual focused beam.

In one alternate embodiment, the ultrasonic transducer array 402 may include a cover portion that presents a circular cross-section. It can be noted that a feature of ultrasonic transducer array 402 is typical in ultrasonic imaging catheters. Due to the severe space restrictions imposed by the small diameter of intracardiac catheters, the ultrasonic transducer array is typically limited to a linear phased array made up of several individual transducer elements, such as 64 transducers or elements. The transducers have a flat surface from which sound is omitted and echoed sound is received. As is well known in the art, the individual transducer elements are pulsed by an ultrasound control system so that the emitted sound waves are constructively combined into a primary beam. By varying the time at which each transducer element is pulsed, the ultrasonic imaging system 300 may render the individual beams into a focused image which can be swept through an arc in order to obtain the 2D image. As a result, the ultrasonic transducer array 402 emits ultrasound along a plane that is perpendicular to the face of the transducer arrays. Thus, the ultrasonic transducer array 402 emits sound along a plane that is perpendicular to the assembly.

Figure 10:
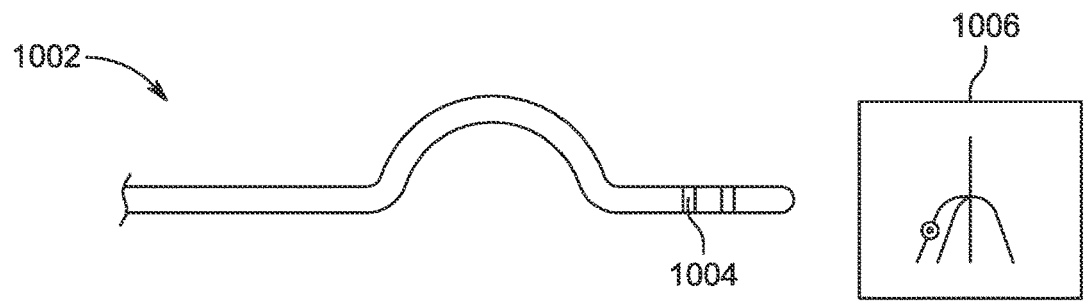
FIG. 10 illustrates a schematic diagram of the ultrasonic catheter having a flexible sheath with a marker band, according to an embodiment of the present disclosure.

Referring to FIG. 10, the ultrasonic catheter 304 may comprise a flexible sheath 1002 with a marker band 1004 to allow location on an X-ray image 1006, according to an embodiment of the present disclosure. The flexible sheath 1002 may have the marker band 1004 towards the distal end 322 of the ultrasonic catheter 304, to allow a passage into the chamber of the heart of the patient and thereby allow location on the X-ray image 1006. It can be noted that the distal end 322 of the ultrasonic catheter 304 may be coated with a material to provide electrical isolation and transmission of ultrasonic signals generated by the ultrasonic catheter 304. In one embodiment, the flexible sheath 1002 may be inserted inside the chamber of the heart and the marker band 1004 may allow location on the X-ray image 1006. It can be noted that the image processor 308 of the ultrasonic imaging device 302 may provide a real-time 2D image of the heart using the allowed location on the X-ray image 1006. In one embodiment, the flexible sheath 1002 may correspond to the catheter shaft 336 to allow the passage into the heart and thereby achieve location on the X-ray image 1006. In one embodiment, the patient's having CF may be treated with the ultrasonic catheter 304 coated with electrical isolation for transmission of ultrasonic signals generated by the ultrasonic catheter 304.

Figure 11:
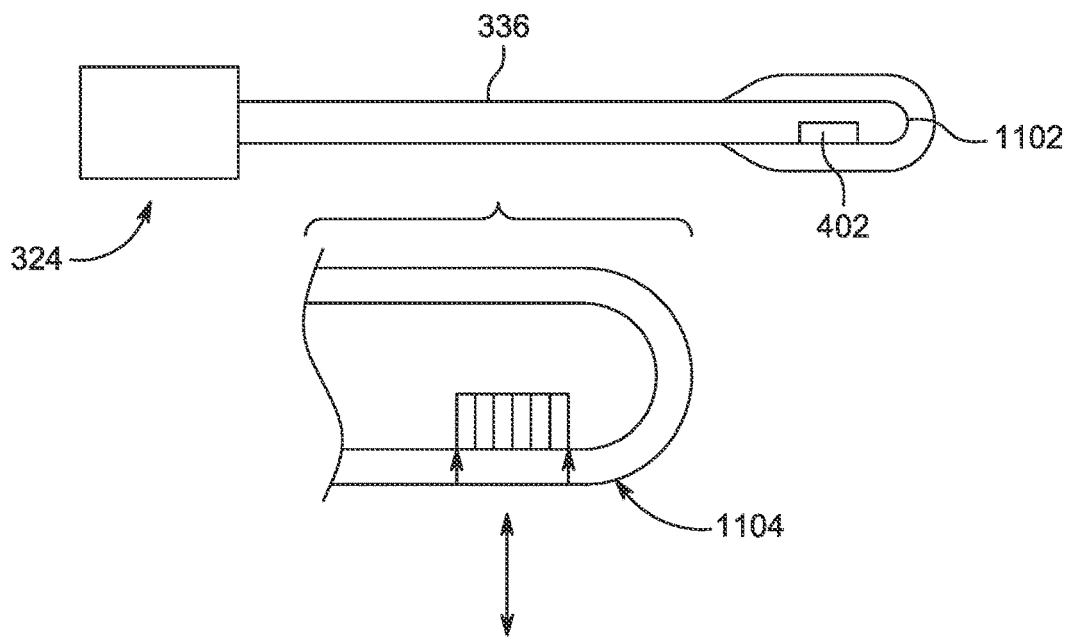
FIG. 11 illustrates a schematic diagram of the ultrasonic catheter having an electrically isolated shaft up to an imaging window at a distal end of the ultrasonic catheter, according to an embodiment of the present disclosure.

Referring to FIG. 11, the ultrasonic catheter 304 may comprise an electrically isolated shaft 1102 towards the distal end 322 of the ultrasonic catheter 304, according to an embodiment of the present disclosure. The electrically isolated shaft 1102 may use a copolymer material up to an imaging window 1104 at the distal end 322 of the ultrasonic catheter 304. In one embodiment, the electrically isolated shaft 1102 may be coated with Pebax material. The imaging window 1104 may allow ultrasound beams to pass back and forth to the ultrasonic transducer array 402. In one embodiment, the steering handle 332 of the steering control unit 326 may be rotated clockwise and/or counter clockwise to a front view or a rear view and thereby, allow the imaging window 1104 to move from a posterior view to an anterior view and/or vice versa. Further, the distal tip 328 of the ultrasonic catheter 304 is coated with an electrically isolated material to provide isolation and transmission of the ultrasound signals.

Figure 12:
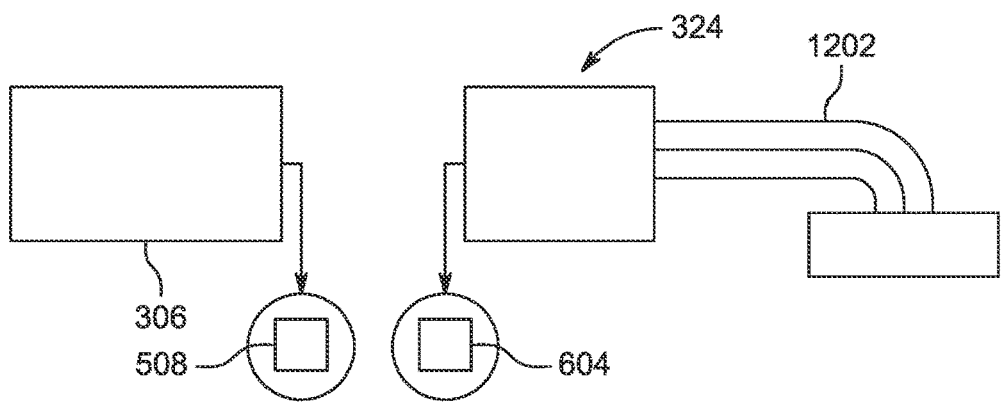
FIG. 12 illustrates a schematic diagram showing a proximal side of a catheter handle assembly coupled to a distal side of a dongle handle assembly using pogo pins and a flat circuit board, according to an embodiment of the present disclosure.

Referring to FIG. 12, an electronic communication between the handle assembly 324 and the custom dongle 306 using the plurality of pogo pins 508, the board edge connectors 606 or other connection means is disclosed, according to an embodiment of the present disclosure. The handle assembly 324 may be coupled with the interposer 406 using the board edge connectors 606 and connector pins 608 which may be coupled to the plurality of inline connection pads 614 of the PCB 610. In one embodiment, the interposer 406 may be referred to as a flat interposer. It can be noted that the interposer 406 may act as a bridge for transmission of the at least one signal from the distal end 322 to the proximal end 320 along the longitudinal axis 318 of the ultrasonic catheter 304. Further, the interposer 406 may be connected to a plurality of electronic flex cables 1202 using the plurality of vias 612. In one embodiment, each of the plurality of electronic flex cables 1202 may have individual connections. Further, the plurality of electronic flex cables 1202 may be connected to the ultrasonic transducer array 402.

In one alternate embodiment, the ultrasonic catheter 304 may comprise a body (not shown) having the longitudinal axis 318 and the distal end 322. Further, the ultrasonic transducer array 402 may be disposed within the distal end of the body. The ultrasonic transducer array 402 may comprise the plurality of transducer array elements 802 arranged on a substrate 326. Further, the ultrasonic transducer array 402 may be connected in series between at least one signal trace and a common ground. Further, each of the plurality of transducer array elements 802 may comprise a plurality of transducers, with a first group of two or more transducers in a first transducer array element and a second group of two or more transducers in the first transducer array element. Further, each of the plurality of transducer array elements 802 may be connected in parallel. Further, each transducer array element may comprise at least one piezoelectric layer disposed on the substrate 326. It can be noted that the at least one piezoelectric layer may comprise the pMUT array element. Further, each transducer array element may comprise at least one first electrode connected between the at least one piezoelectric layer and a signal conductor. Further, at least one-second electrode may be connected between the at least one piezoelectric layer and a ground conductor. In one embodiment, each pMUT array element may have a predetermined geometry configured to accept a predetermined fundamental mode vibration.

In one embodiment, the ultrasonic transducer array may comprise a plurality of Piezoelectric Micromachined Ultrasonic Transducers (pMUTs) coupled at the distal end of the body. It can be noted that the pMUT array is a linear phased array. In one embodiment, the first group of two or more transducers and the second group of two or more transducers may be connected in parallel. Further, the multiple transducer array elements of the plurality of transducer array elements may be grouped to act as a single array element.

Figure 13:
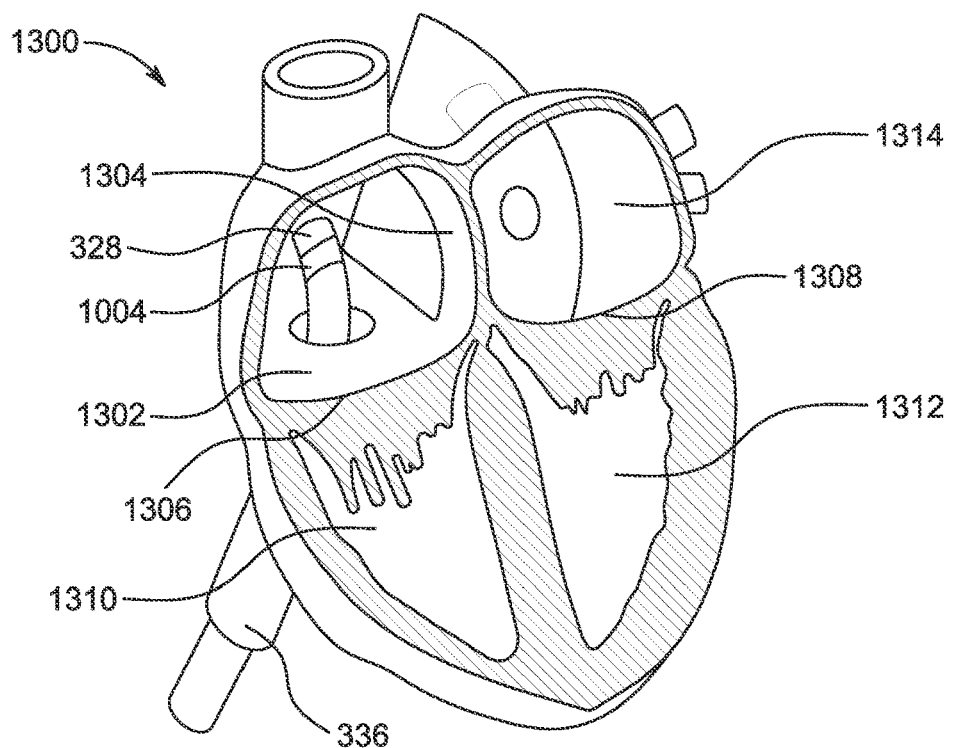
FIGS. 13 and 14 illustrate cross sectional images of a heart with the ultrasonic catheter positioned within a right atrium of the heart, according to an embodiment of the present disclosure.
Figure 14:
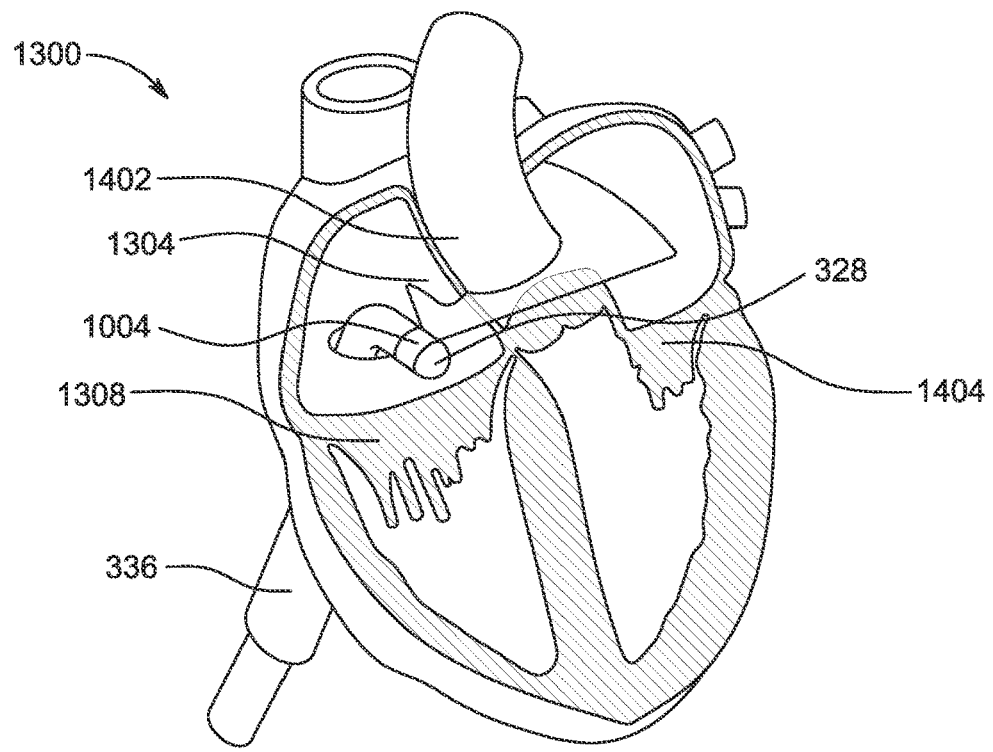

Referring to FIGS. 13-14, cross sectional images of a heart 1300 with the ultrasonic catheter 304 positioned within a right atrium 1302 of the heart 1300, are disclosed. The distal tip 328 of the ultrasonic catheter 304 may be inserted into the right atrium 1302 via an inferior vena cava (not shown). In order to perform an adequate imaging of an interatrial septum (IAS) 1304 and its neighbouring structures, two standardized views may be used. The movement of the distal tip 328 of the ultrasonic catheter 304 within the right atrium 1302 may be controlled by the steering control unit 326. The steering handle 332 of the steering control unit 326 may be rotated to facilitate positioning of the distal tip 328 of the ultrasonic catheter 304 within the heart 1300 of the patient. In one embodiment, the steering handle 332 may be steered clockwise to position the distal tip 328 of the ultrasonic catheter 304 to a rear view of the right atrium 1302. In another embodiment, the steering handle 332 may be steered counter clockwise to position the distal tip 328 of the ultrasonic catheter 304 to a front view of the right atrium 1302. Further, the movement of the steering handle 332 clockwise or counter clockwise, may allow the imaging window 1104 to move from a posterior view to an anterior view or vice versa.

Further, referring to FIGS. 13-14, to properly place the ultrasonic transducer array 402 into position for imaging the right atrium 1302 and a bicuspid valve 1306, the flexible sheath 1002 may be introduced into the patient's vascular structure via a femoral vein (not shown). Using a fluoroscopic imaging to monitor the ultrasonic catheter 304 position, a clinician may advance the distal end 322 of the ultrasonic catheter 304 into the right atrium 1302. In order to guide the ultrasonic catheter 304 through turns in the patient's vascular structure, the clinician may rotate the steering handle 332 clockwise or counter clockwise to allow the imaging window 1104 to move towards the internal views including the anterior position to the posterior position and vice versa. Once the distal tip 328 of the ultrasonic catheter 304 is in the right atrium 1302, the clinician may rotate the steering handle 332 so as to introduce an acute bend in the flexible sheath 1002 to direct the ultrasonic transducer array 402 through a tricuspid valve 1308 and into a right ventricle 1310, as shown in FIG. 13. In this position, a field of view of the ultrasonic transducer array 402 may include portions of the right ventricle 1310, the IAS 1304, a left atrium 1314, the bicuspid valve 1306, the left ventricle 1312, and a left ventricular wall. In one embodiment, when the ultrasonic transducer array 402 is directed by rotating the steering handle 180 degrees clockwise, the right ventricle 1310 and right ventricular wall may be imaged. It can be noted that the clinician may twist the ultrasonic catheter 304, while positioned within the heart 1300 as illustrated in FIGS. 13-14, the transducer array 402 may swing about an axis, which could injure the tricuspid valve 1308 or cause the ultrasonic transducer array 402 to strike the IAS 1304. FIG. 14 shows a perpendicular short-axis view to visualize interior parts of the IAS 1304. The interior parts of the IAS 1304 include an aorta 1402, the IAS 1304, a mitral valve 1404 towards the left ventricle 1312.

In one exemplary embodiment, the standard view is obtained by placing the ultrasonic catheter 304 in a mid-right atrium 1302 and the ultrasonic transducer array 402 in a neutral position facing a tricuspid valve 1308. The standard view provides imaging of the right atrium 1302, the tricuspid valve 1308, right ventricle 1310, and typically an oblique or short-axis view of the aortic valve.

Further, when the ultrasonic catheter 304 may be rotated clockwise the aortic valve in long axis and the right ventricle 1310 outflow tract is viewed. In this view, the tricuspid valve that is closer to the ultrasonic transducer array 402 or the distal tip 328 is a non-coronary cusp, which is in close relationship to a membranous septum and a para-hisian region, whereas the opposite is a right coronary cusp, which is the most anterior of the aortic cusps, directly posterior to the right ventricle 1310 outflow tract infundibulum and pulmonic valve. The left ventricle 1312 is visualized anterior to the most septal portion of the right atrium 1302, and the opening of the coronary sinus becomes evident. In this view, the long axis of the left ventricle 1312 outflow tract is identified, and the posterior left ventricle 1312 is in view just below the non-coronary cusp.

Further, an additional clockwise rotation of the ultrasonic catheter 304 allows visualization of the mitral valve 1404 and the IAS 1304, with the left atrial appendage anteriorly and the coronary sinus posteriorly. The left atrium 1314 appendage is examined for the presence of thrombus at its ostium, and mitral regurgitation may be assessed using a colour Doppler.

In one embodiment, most catheters used in intravascular applications, particularly those with ultrasound transducers, are at least about 10 French in diameter. The electronics and wires needed for ultrasound transducer arrays have made it impractical and expensive to reduce the size of such catheters below about 10 French. Nevertheless, there are benefits in reducing the diameter of the catheter, and technology advances may enable the electronics and control structures to be further reduced in size. The bundling arrangement of the coaxial cables, steering and pivot cables and steering and pivot mechanisms described in more detail below, make it possible to effectively reduce the diameter below about 10 French, to 4, 6, or 8 French or even 3 French (approximately 1 mm).

While there is shown and described herein certain specific structures embodying various embodiments of the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An ultrasonic imaging system comprising:
   an ultrasonic catheter having a longitudinal axis, a proximal end, and a distal end;
   an ultrasonic transducer array disposed within the distal end of the ultrasonic catheter,
     wherein the ultrasonic transducer array comprises a substrate and a plurality of transducer array elements arranged on the substrate; and
   a catheter shaft connected at one end to a handle assembly and at other end to the ultrasonic transducer array, wherein the catheter shaft houses an electronic flex cable which is in communication with at least one signal trace, and is configured to:
     direct each of the plurality of transducer array elements, via the at least one signal trace, to transmit and receive, with respect to heart, ultrasound beams;
     receive at least one signal from the plurality of transducer array elements based on transmitting and receiving at least one ultrasound beam of the ultrasound beams; and
     construct at least one image of at least a portion of the heart based on the at least one signal,
   wherein the ultrasonic catheter is coupled to an imaging device using a dongle, and the dongle is configured to communicate ultrasound transmit pulses and ultrasound receive waveforms between the imaging device and the ultrasonic catheter, wherein:
     the dongle comprises an interposer located at a proximal end of the handle assembly, the interposer having a plurality of connector pins extending from a proximal side and a board edge connector extending from a distal side; and
     the board edge connector is attached to a flat circuit board of the handle assembly that is connected to a plurality of individual electronic flex cables.

2. The ultrasonic imaging system of claim 1, wherein the ultrasonic transducer array corresponds to a micro-electro-mechanical (MEMS) based Piezoelectric Micromachined Ultrasonic Transducer (pMUT).

3. The ultrasonic imaging system of claim 1, wherein the ultrasonic catheter comprises a steering control unit positioned within the handle assembly, for articulating a distal tip of the ultrasonic catheter and aligning face of the ultrasonic transducer array towards internal views including an anterior position or a posterior position of the heart.

4. The ultrasonic imaging system of claim 3, wherein the distal tip of the ultrasonic catheter is coated with a material to provide electrical isolation and transmission of ultrasound signals.

5. The ultrasonic imaging system of claim 3, wherein the steering control unit comprises a housing enclosing an actuator and a steering hub, and an internal friction occurs between the actuator and the steering hub, and between the actuator and the housing, which causes the ultrasonic catheter to retain its adjusted configuration without operator attention.

6. The ultrasonic imaging system of claim 1, wherein the ultrasonic catheter corresponds to a mechanical flexible sheath with a marker band, to allow passage into the heart, and form a location on an X-ray image.

7. The ultrasonic imaging system of claim 1, wherein the catheter shaft encloses the plurality of individual electronic flex cables connected between the handle assembly and the ultrasonic transducer array.

8. The ultrasonic imaging system of claim 1, wherein the ultrasound beams have a bandwidth including a predetermined fundamental mode vibration of each of the plurality of transducer array elements, such that a single array element transmits and receives multiple fundamental mode vibrations simultaneously.

9. The ultrasonic imaging system of claim 1, wherein each of the plurality of transducer array elements has transducer cells of multiple diameters, to achieve a wide bandwidth.

10. An ultrasonic catheter comprising:
a body having a longitudinal axis and a distal end;
an ultrasonic transducer array disposed within the distal end of the body, wherein the ultrasonic transducer array comprises a plurality of transducer array elements arranged on a substrate,
wherein each transducer array element comprises a plurality of transducers, with a first group of two or more transducers in a first transducer array element and a second group of two or more transducers in the first transducer array element, and each transducer array element is connected in parallel, and comprising:
at least one piezoelectric layer disposed on the substrate; at least one first electrode connected between the at least one piezoelectric layer and a signal conductor; and
at least one second electrode connected between the at least one piezoelectric layer and a ground conductor; and
wherein the ultrasonic transducer is configured to be coupled to an imaging device using a dongle, and the dongle is configured to communicate ultrasound transmit pulses and ultrasound receive waveforms between the imaging device and the ultrasonic catheter, wherein:
the dongle comprises an interposer located at a proximal end of the handle assembly, the interposer having a plurality of connector pins extending from a proximal side and a board edge connector extending from a distal side; and
the board edge connector is attached to a flat circuit board of the handle assembly that is connected to a plurality of individual electronic flex cables.

11. The ultrasonic catheter of claim 10, wherein the ultrasonic transducer array corresponds to a micro-electromechanical (MEMS) based Piezoelectric Micromachined Ultrasonic Transducer (pMUT).

12. The ultrasonic catheter of claim 10, wherein each of the plurality of transducer array elements is a linear phased array.

13. The ultrasonic catheter of claim 10, wherein the plurality of transducer array elements creates an individual focused beam.

14. The ultrasonic catheter of claim 10, further comprising an electrically isolated shaft to cover a shaft up to an imaging window at the distal end of the body.

15. The ultrasonic catheter of claim 14, wherein the electrically isolated shaft uses Pebax material to cover the shaft up to the imaging window at the distal end of the body.

16. The ultrasonic catheter of claim 10, wherein the ultrasonic catheter comprises a steering control unit for articulating a distal tip of the ultrasonic catheter and aligning face of the ultrasonic transducer array towards internal views including an anterior position or a posterior position of the heart.

17. The ultrasonic catheter of claim 16, wherein the distal tip of the ultrasonic catheter is coated with a material to provide electrical isolation and transmission of ultrasound signals.

18. The ultrasonic catheter of claim 16, wherein the steering control unit comprises a housing enclosing an actuator and a steering hub, and an internal friction occurs between the actuator and the steering hub, and between the actuator and the housing, which causes the ultrasonic catheter to retain its adjusted configuration without operator attention.

19. An intracardiac echocardiographic (ICE) imaging system comprising:
an ultrasonic catheter having a longitudinal axis, a proximal end, and a distal end;
a micro-electromechanical (MEMS) based Piezoelectric Micromachined Ultrasonic Transducer (pMUT) array disposed within the distal end of the ultrasonic catheter, wherein the MEMS based pMUT array comprises a substrate and a plurality of MEMS based pMUT array elements arranged on the substrate; and
an electronic flex cable connected at one end to a handle assembly and at other end to the MEMS based pMUT array, wherein the electronic flex cable is in communication with at least one signal trace, and is configured to:
direct each of the plurality of MEMS based pMUT array elements, via the at least one signal trace, to transmit and receive, with respect to heart, ultrasound beams;
receive at least one signal from the plurality of MEMS based pMUT array elements based on transmitting and receiving at least one ultrasound beam of the ultrasound beams; and
construct at least one image of at least a portion of the heart based on the at least one signal;
wherein the ultrasonic catheter is coupled to an imaging device using a dongle, and the dongle is configured to communicate ultrasound transmit pulses and ultrasound receive waveforms between the imaging device and the ultrasonic catheter, wherein:
the dongle comprises an interposer located at a proximal end of the handle assembly, the interposer having a plurality of connector pins extending from a proximal side and a board edge connector extending from a distal side; and
the board edge connector is attached to a flat circuit board of the handle assembly that is connected to a plurality of individual electronic flex cables.

20. The ICE imaging system of claim 19, wherein the MEMS based pMUT array comprises pMUT cells of multiple diameters to achieve a bandwidth of greater than 55%.

\* \* \* \* \*